Figure 1:
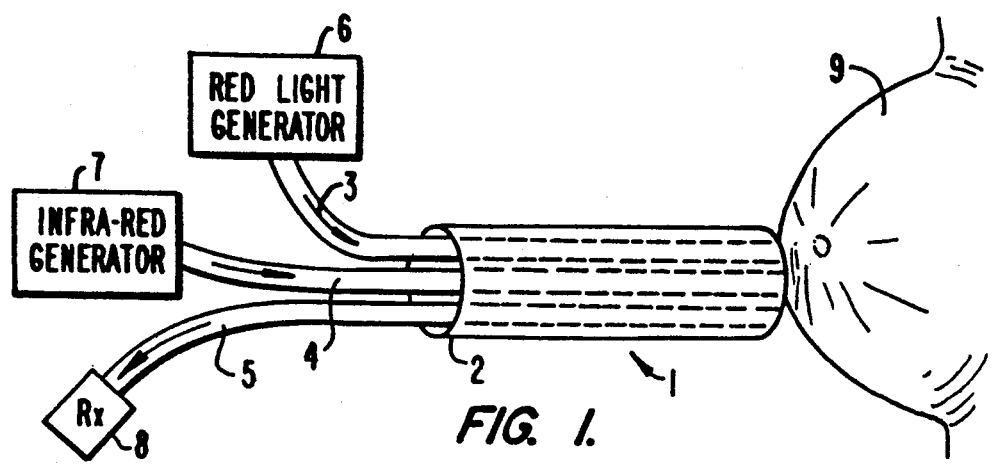

United States Patent [19]

Jeffcoat et al.

[11] Patent Number: 5,036,853
[45] Date of Patent: Aug. 6, 1991

[54] PHYSIOLOGICAL PROBE

[75] Inventors: Keith W. Jeffcoat, Beacon Hill; David W. Bishop, Bayview, both of Australia

[73] Assignee: Polartechnics Ltd., New South Wales, Australia

[21] Appl. No.: 398,365

[22] Filed: Aug. 24, 1989

[30] Foreign Application Priority Data

Aug. 26, 1988 [AU] Australia ............................... PJ0060

[51] Int. Cl.[5] .............................................. A61B 5/00
[52] U.S. Cl. .................................... 128/634; 128/665; 128/633
[58] Field of Search ............... 128/633, 634, 664, 665, 128/691, 694

[56] References Cited

U.S. PATENT DOCUMENTS

| Re. 31,815 | 1/1985 | Alfano | 128/665 |
|---|---|---|---|
| 4,201,222 | 5/1980 | Haase | 128/634 |
| 4,213,462 | 7/1980 | Sato | 128/634 |
| 4,321,930 | 3/1982 | Jobsis et al. | 128/633 |
| 4,407,290 | 10/1983 | Wilber | |
| 4,515,165 | 5/1985 | Carroll | 128/664 |
| 4,541,438 | 9/1985 | Parker et al. | 128/664 |
| 4,653,498 | 3/1987 | New, Jr. et al. | 128/633 |
| 4,714,080 | 12/1987 | Edgar | |
| 4,718,417 | 1/1988 | Kittrell et al. | 128/634 |
| 4,796,636 | 1/1989 | Branstetter et al. | 128/633 |
| 4,846,183 | 7/1989 | Martin | 128/633 |
| 4,867,557 | 9/1989 | Takatani et al. | 128/633 |

FOREIGN PATENT DOCUMENTS 0099756 7/1983 European Pat. Off. .
2162939 7/1985 United Kingdom .

Primary Examiner—Lee S. Cohen
Assistant Examiner—John D. Zele
Attorney, Agent, or Firm—Townsend and Townsend

[57] ABSTRACT

A method of, and apparatus for, identifying human tissue which is suspected of being physiologically changed as a result of commencement of neoplastic activity or pre-activity, is disclosed. The tissue is preferably irradiated with light at wavelengths of 660 nm and 940 nm. The magnitudes of the reflected, or non-absorbed, light at the two wavelengths is compared, preferably after being normalized by the magnitude of ambient light reflected from the tissue immediately prior to each measurement. The invention finds application in detecting cervical lesions but is also applicable to endoscope inspectable tissues such as the lungs and alimentary canal tissues.

11 Claims, 2 Drawing Sheets

PHYSIOLOGICAL PROBE

The present invention relates to a physiological probe for identifying tissue which is suspected of being physiologically changed as a result of commencement of neoplastic activity or pre-activity.

Although the preferred embodiment of the present invention to be described hereafter has particular application to cervical lesions, the present invention is also applicable to lesions of various tissues which can be inspected by means of an endoscope, for example, which can be inserted into the lungs, into the abdominal canal, or into the rectum. Thus the present invention is not generally applicable to tissues of interior organs such as the liver or kidneys.

It is believed that by doing a spectral analysis of the tissue an indicator of cancerous or precancerous activity can be found.

When viewed under white light, this cancerous or precancerous activity makes itself apparent by increased redness of the tissue. However, because there is a wide variety of perceived color, bought about by the reflection, or non-absorption, of light by tissue, it is not possible to accurately predict the presence or absence of neoplastic activity simply based on the color of the tissue alone.

Although white light is convenient to use, white light represents only a very small band of wavelengths of electromagnetic radiation in the range of, say, from 200 nm to 12,000 nm which may be loosely classed as having properties similar to that of light. This band of wavelengths includes ultraviolet light, visible light and infra red radiation. It is generally desirable to work with a wavelength close to visible light since the further one moves away from this band of wavelengths, the more difficult and complicated the apparatus generally becomes. A major advantage of electromagnetic radiation in this region is that it is not effected by, for example, mucus present on the cervix.

For many years the presence of cervical cancer has been detected using a process known as the Pap Smear. This is a chemical test which relies upon the collection of a sample of material immediately adjacent the opening of the cervix. This test is not as reliable as it might be because of variations introduced by the ability of the operator to accurately take a sample, the need for the sample to be sent away to a laboratory for analysis where the sample is viewed under magnification by an operator who makes a subjective assessment of the tissue.

If a positive result is produced, the patient is then examined by means of a colposcope which enables a magnified view of the cervix to be examined by a skilled practitioner who makes a subjective judgement of the tissue observed. Any suspect regions of the cervix can then be burnt away using a laser, for example, and the cervical tissue then re-grows. Such easy preventative treatment is only possible if the lesion is detected at an early stage. Since Pap Smears are normally conducted on an annual basis, a faulty test during one year can mean that a lesion is not detected until the following year, at the earliest.

It is the object of the present invention to substantially overcome, or ameliorate, the disadvantages inherent in Pap Smear testing by the provision of a physiological probe which enables a substantially instantaneous and objective indication of the presence or absence of neoplastic activity to be provided.

The essential advance inherent in the present invention is the measurement of the magnitude of electromagnetic radiation in the near light region mentioned above reflected from the tissue at two different wavelengths. The ratio of the reflected magnitudes appear to provide a reliable indication of the presence or absence of neoplastic activity.

According to the present invention there is disclosed a physiological probe for identifying cervical tissue which is suspected of being physiologically changed as a result of commencement of neoplastic activity or pre-activity of a cervical lesion, said probe having one end shaped to face said cervical tissue and comprising at least two paths for electromagnetic radiation in the range of from 200 nm to 12,000 nm, at least one of said paths leading to said one end and arranged to convey said electromagnetic radiation in a first direction towards said one end, and at least one of said paths leading from said one end and arranged to convey said electromagnetic radiation in a second direction away from said one end;

a first electromagnetic generator means connected to said at least one first direction path to transmit said electromagnetic radiation at a first wavelength within said range along one of said first direction paths and a second electromagnetic generator means connected to said at least one first direction path to transmit said electromagnetic radiation at a second wavelength within said range along one of said first direction paths, said second wavelength being different from said first wavelength;

receiver means connected to said at least one second direction to receive said radiation at said first and second wavelengths reflected by said tissue, and comparator means to generate the ratio of the magnitudes of said received radiation and compare same with known ratios to thereby identify tissue condition.

In one form two paths only are provided. A single receiver and two generators are provided with the generators transmitting alternatively. If preferred two receivers can be provided and switched to operate from the single return path.

In another form three paths are provided. A single receiver is connected to the return path and each generator is connected to a corresponding sending path. In a further form four paths are provided with two receivers each connected to a corresponding return path.

Figure 2:
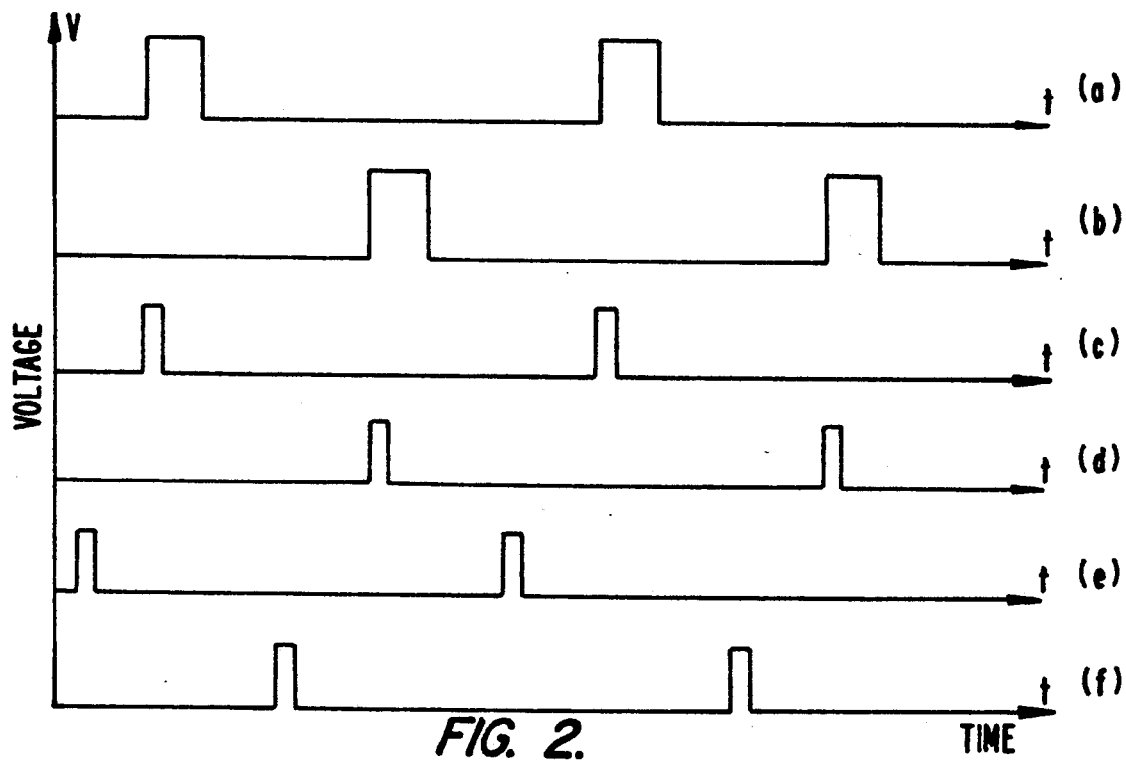
Figure 3:
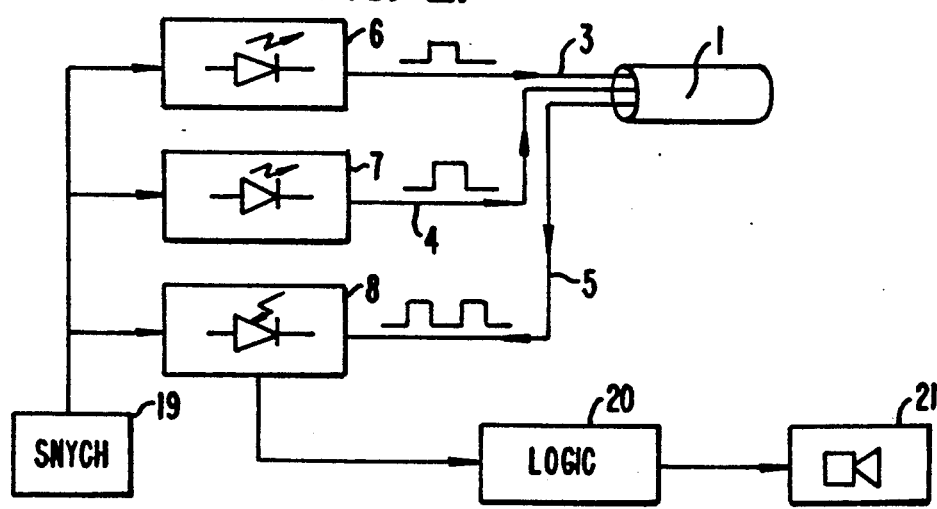
Figure 4:
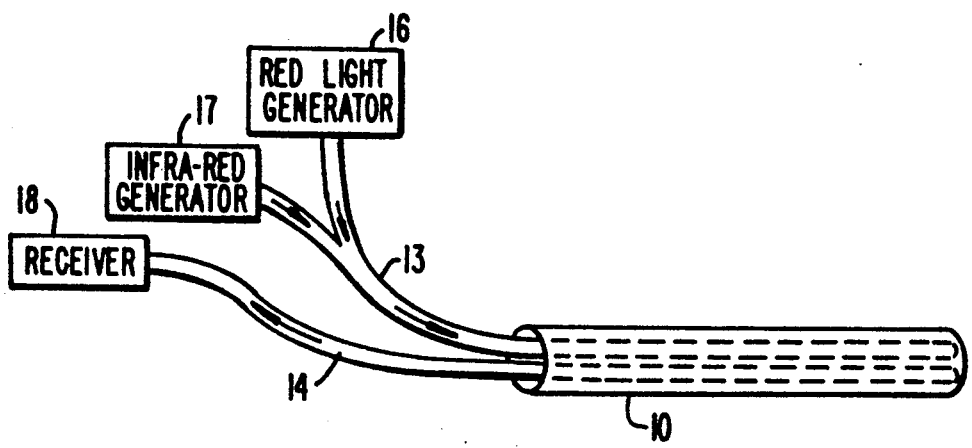
Figure 5:
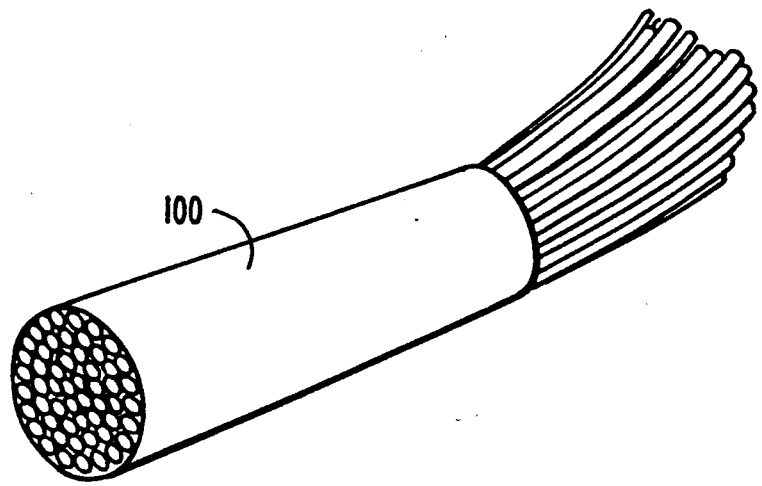
Figure 6:
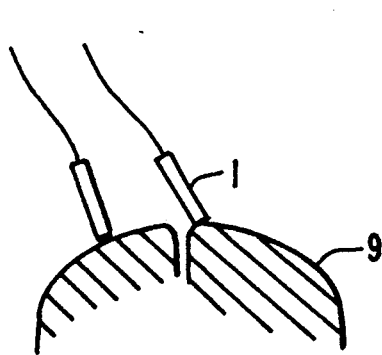
Figure 7:
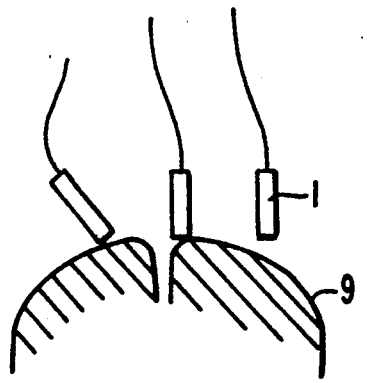

Embodiments of the present invention will now be described with reference to the drawings in which:

FIG. 1 is a schematic representation of the probe of the preferred embodiment approaching contact with the tissue of a cervix, FIGS. 2(a-f) is a graph of the timing relationships of the apparatus of FIG. 1, FIG. 3 illustrates in schematic form the circuit arrangement required to realize the apparatus of FIG. 1, FIG. 4 is a view similar to FIG. 1 but illustrating an alternative arrangement of paths, FIG. 5 is a view of a probe of a further embodiment illustrating a still further arrangement of optical paths, and FIGS. 6 and 7 are schematic cross-sectional views of a cervix illustrating respectively the correct and Incorrect probe attitudes.

Turning now to FIG. 1 the probe 1 of the preferred embodiment comprises a generally cylindrical housing 2 for three optical fibers 3–5.

Optical fiber 3 is a sending path and connects to the probe 1 a red light generator 6 which can operate in the range of from 650 nm to 850 nm but which preferably operates at approximately 660 nm. Similarly, optical fiber 4 is also a sending path and connects to the probe 1 an infra-red generator 7 operating in the range of from 850 nm to 1000 nm but preferably operates at a near infrared wavelength of 940 nm. However, optical fiber 5 is a return path which connects the probe 1 to a receiver 8. Alternatively the generator and detector devices can be on the probe tip for direct coupling to the tissue without the intervention of optical fibers.

FIG. 3 illustrates in schematic form a practical realization of the apparatus of FIG. 1. The generators 6 and 7 are realized by LED optical transmitters whilst the receiver 8 is realized by a photo diode receiver. A synchronizing circuit 19 controls the operation of the generators 6, 7 and receiver 8. The output of the receiver 8 is passed to a logic circuit 20 for processing which in turn triggers an alarm 21 as required.

With the tips of the fibers 3 and 5, and hence the tip of the probe 1, in contact with the tissue of the cervix 9, red light is first passed from generator 6 down optical fiber 3 and a portion thereof is reflected along return path 5 and received at the receiver 8.

The timing diagrams used in the circuit of FIG. 3 are illustrated in FIG. 2. The upper trace (a) represents the pulses of red light emitted by generator 6 in accordance with the signals provided to it by the synchronizing circuit 19. Similarly, the second trace (b) from the top represents the pulses of infra red light emitted by generator 7.

The third trace (c) from the top illustrated in FIG. 2 is applied to the receiver 8 and enables the receiver 8 to sample the intensity of light created by the generator 6 and thus constitutes a red signal magnitude. Similarly, the next trace (d) is also applied to the receiver 8 and samples the magnitude of infra red light generated or emitted by generator 7. Thus an infra red signal magnitude is sampled by the receiver 8. Both signals are stored in the logic circuit 20.

The penultimate trace (e) when applied to the receiver 8 permits the ambient light reflected from the tissue of the cervix 9 to be passed along optical fiber 5 to be sampled. Thus the magnitude of the reflected ambient light (termed red base radiation), before the red reflected light is sampled, is also stored in the logic circuit 20. Finally, the last trace (f) in FIG. 2 illustrates the waveform applied to the receiver 8 in order to sample the ambient radiation reflected from the tissue of the cervix (termed infra red base radiation), before the infra red light is sampled.

The logic circuit 20 generates a ratio formed by the difference between the sampled reflected red radiation and the sampled base red radiation, divided by the sampled reflected infra red radiation less the magnitude of the sampled base infra red radiation.

If this ratio is approximately 1, this indicates that the tissue is normal. If the ratio is approximately 10 to 20% higher this indicates that the tissue is undergoing change which suggests neoplasia or pre-neoplasia metaplastic and if the ratio is approximately 20 to 50% lower then this indicates necrotic tissue suggestive of an advanced neoplasm.

In this connection, it will be appreciated that the signals from the receiver 8 are preferably filtered with a filter having a time constant of the order of 12 ms so that any oscillations occurring within this time are averaged. As the pulse repetition rate of the signals from the synchronizing circuit 19 is approximately 500 Hz, this enables any noise due to the movement of the probe over tissue, or short term perturbations of the signals, and the like to be filtered out.

It has been found that two wavelengths are required because the reflection, or absorption of a given wave length of "light" changes with time, largely due to the patient's pulse, and also with the location of the probe on the cervix. However, the ratio of the normalized magnitudes of the reflected "light" at two wavelengths appears to be substantially constant for a given type of tissue.

In this connection, it has been found that neoplastic change in tissue shows as a change in dielectric, which in turn gives a change In reflectivity. Early neoplastic change of tissue has a higher reflectivity or red light than normal cells.

Conversely, the cells of necrotic tissue at the center of advanced neoplastic tissue have a negligible or poor blood supply and therefore have a very low red reflectivity.

It is desirable that the logic circuit 20 be arranged so that if the ratio exceeds 10 to 20% above normal a first audible alarm is sounded, if the ratio falls 20 to 50% below normal a second audible alarm is sounded and that if both conditions are experienced within a predetermined period of time, indicative of the probe moving from one extreme type of cancerous tissue to the other, then a third audible alarm is sounded. Such audible alarms are useful because the probe can be operated alongside a colposcope and thus the operator of the colposcope is watching the cervix thereof and his eyes are fully occupied and unable to appreciate the flashing, for example, of an alarm light or other means of visual information.

Turning now to FIG. 4, a second embodiment of the physiolgical probe of the present invention is schematically illustrated. In this probe 10 a single sending path 13 to which both generators 16 and 17 are connected is provided. The return path 14 to which receiver 18 is connected is substantially the same.

It will be apparent that the timing arrangements for the probe 10 of FIG. 4 are substantially similar to that of the probe 1 of FIGS. 1 and 3 except that the red and infra red radiation passes sequentially along the single sending optical path 13.

An alternative arrangement with dual receivers which are responsive only to a given one of the two wavelengths will be apparent to those skilled in the art. Such dual receivers can both be connected to a single return path, or alternatively be connected to individual return paths. FIG. 5 illustrates a further embodiment of the probe 100 which includes a bundle of optical fibers and thereby permits data as to the spacial location of the area of tissue types of interest, to be determined, for example with reference to the center of the cervix.

FIG. 6 illustrates two correct positions for abutting the probe 1 against the cervix 9. In each instance, it is essential to avoid spurious readings for the probe 1 to be substantially normal to the surface of the cervix.

By way of contrast, FIG. 7 illustrates three erroneous positions of the probe 1 which may give rise to misleading or spurious indications. These erroneous positions essentially are that the probe 1 is not normal to the surface of the cervix and/or that the probe 1 is not actually touching the surface of the cervix.

The foregoing describes only some embodiments of the present invention and modifications, obvious to those skilled in the art, can be made thereto without departing from the scope of the present invention.

We claim:

1. A physiological probe for identifying cervical tissue which is suspected of being physiologically changed as a result of commencement of neoplastic activity or pre-activity of a cervical lesion, said probe having one end shaped to face said cervical tissue and comprising at least two paths for electromagnetic radiation in the range of from 200 nm to 12,000 nm, at least one of said paths leading to said one end arranged to convey said electromagnetic radiation in a first direction towards said one end, and at least one of said paths leading from said one end and arranged to convey said electromagnetic radiation in a second direction away from said one end;

a first electromagnetic generator means connected to said at least one first direction path to transmit said electromagnetic radiation at a first wavelength within said range along said at least one first direction path and a second electromagnetic generator means connected to said at least one first direction path to transmit said electromagnetic radiation at a second wavelength within said range along said at least one first direction path, said second wavelength being different from said first wavelength;

receiver means connected to said at least one second direction path to receive said radiation at said first and second wavelengths reflected from said cervical tissue, and comparator means to generate the ratio of the magnitudes of said received radiation and compare same with known ratios to thereby identify cervical tissue condition.

2. A probe as claimed in claim 1 wherein said receiver means receives ambient light reflected from said cervical tissue and said comparator means generates a ratio formed by the difference between the magnitude of the received ambient light and the magnitude of the received first wavelength radiation, divided by the difference between the magnitude of the received ambient light and the magnitude of the received second wavelength radiation.

3. A probe as claimed in claim 2 wherein said first and second electromagnetic generator means and receiver means are controlled by a timing means to respectively generate timed pulses of said first and second wavelengths and activate said receiver means to determine both the magnitude of the received pulses of said first and second wavelengths and the magnitude of said received ambient light just prior to receipt of said received pulses.

4. A probe as claimed in claim 3 wherein at least two of said first direction paths for electromagnetic radiation are provided, said first generator means being connected to one of said first direction paths and said second generator means being connected to another of said first direction paths, said generators being connected to the end of said paths remote from said one end of said probe.

5. A probe as claimed in claim 3 wherein said first and second generator means are both connected to the same first direction path at the end thereof remote from said one end of said probe, and said timing means being arranged to generate said first and second wavelength pulses in sequence.

6. A probe as claimed in claim 1 wherein said paths for electromagnetic radiation comprise optical fibers, said first wavelength is in the range of from 650 nm to 850 nm, said second wavelength is in the range of from 850 nm to 1000 nm, and an alarm is connected to the comparator means, said alarm being activated if said ratio diverges from approximately unity.

7. A method of identifying cervical tissue which is suspected of being physiologically changed as a result of commencement of neoplastic activity or pre-activity, said method comprising the steps of:

irradiating said cervical tissue with electromagnetic radiation at a first wavelength;

irradiating said cervical tissue with electromagnetic radiation at a second wavelength, said first and second wavelengths being different and within the range of from 200 nm to 12,000 nm;

receiving the radiation at said first and second wavelengths reflected by said cervical tissue;

generating the ratio of the magnitudes of said received radiation; and identifying the condition of said cervical tissue by comparing said generated ratios with known ratios.

8. A method as claimed in claim 7 including the step of receiving ambient light reflected by said cervical tissue, and measuring the ratio formed by the difference between the magnitude of the received ambient light and the magnitude of the received first wavelength radiation, divided by the difference between the magnitude of the received ambient light and the magnitude of the received second wavelength radiation.

9. A method as claimed in claim 8 wherein each said difference is formed by the magnitude of the received ambient light measured just before the measurement of the received first or second wavelength radiation.

10. A method as claimed in claim 9 wherein said cervical tissue is irradiated with timed pulses of said first and second wavelength radiation.

11. A method as claimed in claim 10 wherein said first wavelength is in the range of from 650 nm to 850 nm and said second wavelength is in the range of from 850 nm to 1000 nm.

* * * * *